United States Patent [19]

DeRosa et al.

[11] Patent Number: 5,226,925
[45] Date of Patent: Jul. 13, 1993

[54] COMPOSITION OF MATTER FOR ALLOPHANATE ENCAPSULATION IN AN AROMATIC-ALIPHATIC

[75] Inventors: Thomas F. DeRosa, Passaic, N.J.; Rodney L. Sung, Fishkill; Benjamin J. Kaufman, Hopewell Junction, both of N.Y.

[73] Assignee: Texaco Inc., White Plains, N.Y.

[21] Appl. No.: 955,005

[22] Filed: Oct. 1, 1992

[51] Int. Cl.$^5$ ............................ C10L 1/22; C01B 21/00
[52] U.S. Cl. .......................................... 44/417; 423/235
[58] Field of Search ........................... 44/417; 423/235

[56] References Cited

U.S. PATENT DOCUMENTS

| | | | |
|---|---|---|---|
| 4,770,863 | 9/1988 | Epperly et al. | 423/235 |
| 4,908,193 | 3/1990 | Perry | 423/235 |
| 4,927,612 | 5/1990 | Bowers | 423/235 |
| 5,017,347 | 5/1991 | Epperly et al. | 423/235 |

*Primary Examiner*—Jerry Johnson
*Attorney, Agent, or Firm*—James J. O'Loughlin; Vincent A. Mallare

[57] ABSTRACT

A composition of matter comprising a mixture of:
a) p-nonyl-co-p-phenylcalix[8]arene monoallophanate;
b) p-nonyl-co-p-phenylcalix[8]arene diallophanate;
c) p-nonyl-co-p-phenylcalix[8]arene triallophanate;
d) p-nonyl-co-p-phenylcalix[8]arene tetraallophanate;
e) p-nonyl-co-p-phenylcalix[8]arene pentallophanate;
f) p-nonyl-co-p-phenylcalix[8]arene hexaallophanate;
g) p-nonyl-co-p-phenylcalix[8]arene heptaallophanate; and
h) p-nonyl-co-p-phenylcalix[8]arene octaallophanate.

1 Claim, No Drawings

COMPOSITION OF MATTER FOR ALLOPHANATE ENCAPSULATION IN AN AROMATIC-ALIPHATIC

BACKGROUND OF THE INVENTION

This composition of matter relates to a chemical method of decreasing nitric oxide, Nox, levels. The chemical method utilizes chemical materials and methods that are well known in the art. The chemicals utilized by this composition of matter patent are reducing agents. When these reducing agents come in contact with NOx, the latter is reduced to non-toxic or environmentally friendly substances. The chemical method utilized in this composition of matter patent entails encapsulating or incorporating the reducing agent into a passive or non-reactive cavity. Moreover, encapsulating the reagent is designed to both enhance the overall thermal stability of the reducing agent and to foster its dissolution in diesel fuel.

Nitrogen oxides are the oxidation products of elemental nitrogen, organic, or inorganic nitrogen and oxygen at elevated temperatures. Nitrogen oxides include nitric oxide, NO; nitrogen dioxide, NO2; nitrogen trioxide, NO3; dinitrogen trioxide, N2O3; tetranitrogen pentaoxide, N4O5; tetranitrogen hexaoxide, N4O6; nitrous oxide, N2O; and the like. Elevated temperatures required to prepare these oxidation products are routinely obtained in internal combustion engines utilizing gasoline, diesel, or aviation fuel.

There are cogent ecological and environmental reasons to reduce or ideally eliminate NOx as an internal combustion oxidation product. Once produced, NOx is directly responsible for acid rain and photochemical smog. Moreover, chronic exposure to NOx has been directly linked with restricted pulmonary compliance in non-smoking healthy males; acute respiratory disease among children living in "high exposure" towns in Czechoslovakia; and a key irritant cited for the high incidence of chronic bronchitis among Japanese postal workers servicing urban centers as outlined in Medical and Biologic Effects of Environmental Pollutants by the National Academy of Sciences, 1977.

DISCLOSURE STATEMENT

Numerous physical methods have been suggested to reduce or eliminate NOx. Certain proposed techniques involve a great deal of capital outlay and require major consumption of additives, scrubbers, etc. For example, U.S. Pat. No. 3,894,141 proposes a reaction of NOx with liquid hydrocarbons; U.S. Pat. No. 4,405,587 proposes high temperature burning of NOx with a hydrocarbon; U.S. Pat. No. 4,448,899 proposes reacting of NOx with an iron chelate; U.S. Pat. No. 3,262,751 reacts NOx with a conjugated olefin. Other methods utilize reactions of NOx with nitriles (U.S. Pat. No. 4,080,425). Application of these reactions imposes organic pollutant disposal problems along with the attendant problems of toxicity and malodorous environments. In addition, they require the presence of oxygen and are relatively expensive. Other systems are based on urea reactions. For example U.S. Pat. No. 4,119,702 discloses the use of a combination of urea and an oxidizing agent which decomposes it, e.g., ozone, nitric acid, inter alia; U.S. Pat. No. 4,325,924 utilizes urea in a high temperature reducing atmosphere; and U.S. Pat. No. 3,900,554 (the thermodenox system) utilizes a combination of ammonia and oxygen to react with nitric oxide. All of these methods must deal with the problem of ammonia and its disposal. All require oxygen and other oxidizing agents. These methods also suffer from the drawback of requiring controlled environments which make them difficult to use in mobile vehicles or smaller stationary devices.

Back et al, Can J.Chem. 46, 531 (1968), discusses the effect of NOx on the photolysis of isocyanic acid, HNCO, the decomposition product of cyanuric acid. Increased nitrogen levels in the presence of nitric oxide were observed utilizing a medium pressure mercury lamp for HNCO photolysis. Despite several remaining uncertainties, it was clear that nitric oxide levels were reduced when contact with isocyanic acid. A readily available of isocyanic acid is via the thermal decomposition or unzipping of the corresponding trimer, cyanuric acid, (HNCO)3.

Other disclosures, especially as noted by Epperly et al in U.S. Pat. Nos. 4,770,863 and 5,017,347 and Bowers in U.S. Pat. No. 4,927,612 report the use of allophanates as another source of isocyanic acid. These methods also have limited applicability in non-stationary power generators because of their very limited solubility in non-polar solvents, most notably, diesel fuel.

Thus, an object of the present invention is to provide a chemical preparation of isocyanic acid from a material that is a diesel fuel-soluble precursor for non-stationary power generators.

SUMMARY OF THE INVENTION

This invention provides a composition of matter comprising a mixture of:
a) p-nonyl-co-p-phenylcalix[8]arene monoallophanate;
b) p-nonyl-co-p-phenylcalix[8]arene diallophanate;
c) p-nonyl-co-p-phenylcalix[8]arene triallophanate;
d) p-nonyl-co-p-phenylcalix[8]arene tetraallophanate;
e) p-nonyl-co-p-phenylcalix[8]arene pentallophanate;
f) p-nonyl-co-p-phenylcalix[8]arene hexaallophanate;
g) p-nonyl-co-p-phenylcalix[8]arene heptaallophanate; and
h) p-nonyl-co-p-phenylcalix[8]arene octaallophanate.

DETAILED DISCUSSION OF THE INVENTION

The present invention provides a composition of matter comprising a mixture of eight components. The process for producing such components, i.e., reaction products, entails reacting a calixarene structurally represented as

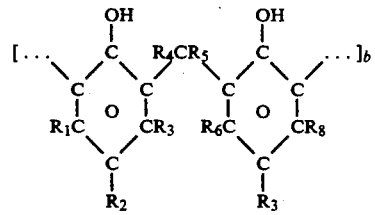

where $R_1$, $R_2$, $R_3$, $R_4$, $R_5$, $R_6$, and $R_8$ are each hydrogen or a $(C_1-C_{50})$ linear, branched, saturated or unsaturated hydrocarbon; and b is an integer between 1 and 8. Moreover, it has been determined that calixarenes derived from p-nonylphenol and p-phenylphenol achieve crucial material requirements. For clarity, calix[2b]arene may be more conveniently represented in a structurally abridged form

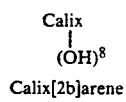

and isocyanic acid produced by the thermal decomposition of urea to generate calixarene allophanates represented by:

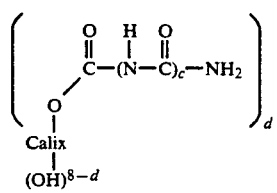

where d is representative of the allophanate repeat unit and is an integer of between 0 and 5, but it is especially desirable to limit d to 1. A summary of the reaction products which make up the components of the composition of matter of this invention is provided below.

| Code | d | Product Name |
|---|---|---|
| $C_0$ | 0 | (Unmodified) p-nonyl-co-p-phenylcalix[8]arene |
| $C_1$ | 1 | p-nonyl-co-p-phenylcalix[8]arene monoallophanate |
| $C_2$ | 2 | p-nonyl-co-p-phenylcalix[8]arene diallophanate |
| $C_3$ | 3 | p-nonyl-co-p-phenylcalix[8]arene triallophanate |
| $C_4$ | 4 | p-nonyl-co-p-phenylcalix[8]arene tetraallophanate |
| $C_5$ | 5 | p-nonyl-co-p-phenylcalix[8]arene pentallophanate |
| $C_6$ | 6 | p-nonyl-co-p-phenylcalix[8]arene hexaallophanate |
| $C_7$ | 7 | p-nonyl-co-p-phenylcalix[8]arene heptaallophanate |
| $C_8$ | 8 | p-nonyl-co-p-phenylcalix[8]arene octaallophanate |

The composition of matter of this invention is directed to two crucial areas: solubilization of allophanates in diesel fuel and the thermal enhancement of the same in order to survive the combustion event of an internal combustion engine. It has now been found that the encapsulation of allophanates in a calixarene cavity achieves these criteria. The chemical method according to the present invention utilizes two key materials, which, when used independently are completely ineffective in reducing nitric oxides. In one case, one material is completely insoluble in diesel fuel; while in the other, the crucial intermediate is not generated. The intrinsic chemical property exploited for each of these materials is provided below.

a) Alkyl-co-Aromaticcalix[8]arene: Completely miscible in diesel.
b) Alkyl or Aromatic Allophanates: Upon thermal decomposition generates the nitric oxide reducing agent, isocyanic acid, HNCO.

The chemical underpinning of this invention is generating isocyanic acid, HNCO, to reduce nitrogen oxide emissions to environmentally friendly materials as depicted below (Eq. 1). Isocyanic acid is generated quantatively by thermally decomposing cyanuric acid as shown below (Eq. 2).

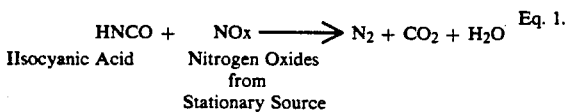

Eq. 1.

However, cyanuric acid technology has very limited applicability to non-stationary NOx power plants because of its insolubility in diesel fuel. Moreover, attempts to solubilize it in diesel fuel suffer from two fundamental flaws:

a) Replacement of one or more of its acidic protons reduces the amount of cyanuric acid generated below (Eqs. 3,4, and 5); and
b) Solubilization of cyanuric acid in diesel fuel cannot assure its survival during the internal combustion event.

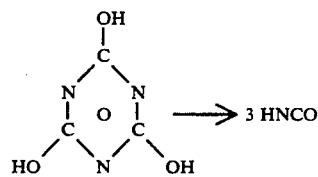

Eq. 2.

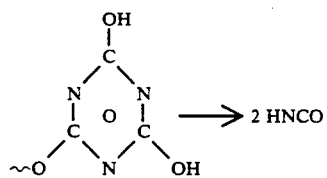

Eq. 3.

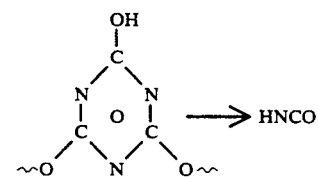

Eq. 4.

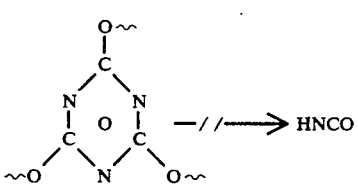

Eq. 5.

The thrust of the present invention is both the ability to utilize allophanate (I) as another isocyanic source (Eq. 6.) and to cause dissolution of the same by chemically encapsulating the allophanate (I) in a calixarene. In the structural depiction of a substituted allophanate below, R represents a homo-, co-, tere-, or tetacalixarene while a represents an integer from 0 to 3.

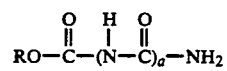

Substituted Allophanate (I)

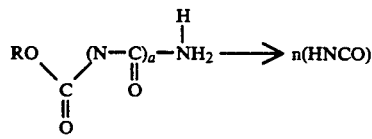

Eq. 6.

Moreover, a second thrust of this invention is our empirical determination that by partial or full encapsulation of the allophanate in a calixarene cavity (II), enhanced thermal stability results.

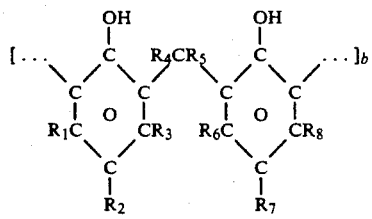

Calix [2b]arene
(II)

In the structural representation of calixarenes amenable to this invention provided above, $R_1$, $R_2$, $R_3$, $R_4$, $R_5$, $R_6$, and $R_8$ are each hydrogen or a ($C_1$–$C_{50}$) linear, branched, saturated or unsaturated hydrocarbon; $R_7$ is a mono-, di-, or polyaromatic substituted or unsubstituted; and the cavity size, b, is an integer of between 1 and 8. According to the present invention, it has been determined that calixarenes derived from p-nonylphenol and p-phenylphenol have optimized diesel fuel solubility and thermal stability as provided below (III)

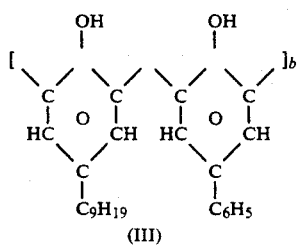

(III)
p-nonyl-co-p-phenylcalix[2b]arene

For clarity wherever possible herein calixarene (II) is more conveniently represented by the abbreviated structure shown below (IV). The present method of incorporating allophanates into the calixarene cavity utilizes urea. Thermal decomposition of urea generates the reactive intermediate, isocyanic acid, HNCO (Eq. 7).

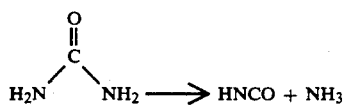
Eq. 7.

Performing this decomposition reaction in the presence of calixarenes generates the partial or fully encapsulated allophanates mixture. Moreover, the amount encapsulated allophanate may be varied by skewing the molar ratio of reagents. Thus according to the present invention, an encapsulation mixture allophanates is produced as generically depicted (V) below in Eq. 8. The generic nomenclature and structural summaries of the product mixture depicted in Eq. 8. are provided below in Table I.

```
    Calix
     |
   (OH)8
    (IV)
```

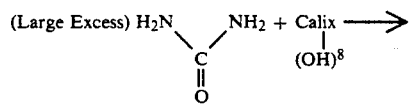
EQ. 8.

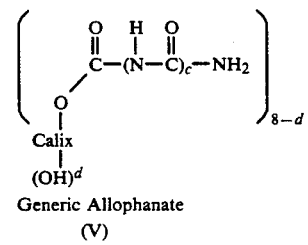

Generic Allophanate
(V)

TABLE I

| Calixarene Allophanate Product Summary Generated By Reacting Urea And P-nonyl-co-P-phenylcalix[8]arene | |
|---|---|
| p-Nonyl-co-p-Phenylcalix[8]arene Allophanate | d |
| p-nonyl-co-p-phenylcalix[8]arene | 0 |
| p-nonyl-co-p-phenylcalix[8]arene monoallophanate | 1 |
| p-nonyl-co-p-phenylcalix[8]arene diallophanate | 2 |
| p-nonyl-co-p-phenylcalix[8]arene triallophanate | 3 |
| p-nonyl-co-p-phenylcalix[8]arene tetraallophanate | 4 |
| p-nonyl-co-p-phenylcalix[8]arene pentallophanate | 5 |
| p-nonyl-co-p-phenylcalix[8]arene hexaallophanate | 6 |
| p-nonyl-co-p-phenylcalix[8]arene heptaallophanate | 7 |
| p-nonyl-co-p-phenylcalix[8]arene octaallophanate | 8 |

In order to further illustrate the present invention and its advantages, the following examples are provided. It is understood, however, that this does not limit the scope nor the application of the present invention.

EXAMPLE I

Preparation of p-Nonylcalix[8]arene

A three neck round bottom equipped with a magnetic stirrer, thermometer, and reflux condenser with a Dean-Stark adapter was charged with 30 parts p-n-nonylphenol, 400 parts, xylene, 1 part sodium hydroxide, and 8 parts paraformal-dehyde and heated to reflux for 48 hours. Sufficient hydrochloride acid was added to neutralize the residue base and the mixture vacuum distilled to remove the unreacted reagents and solvent to provide the present resinous material. The present product was redissolved in xylene and precipitated in a copious amount of 1:1 v/v methanol-water mixture, respectively

EXAMPLE II

Preparation of p-Nonyl-Co-p-PhenylCalix[8]arene

In this example, a 2.5 mole-mole ratio of p-phenylphenol and p-n-nonyl-phenol, respectively, was substituted for the p-n-nonylphenol of Example 1, above, and the procedure thereof was used herein to produce the product of this example.

EXAMPLE III

Preparation of p-Nonyl-Co-p-phenylCalix[8]arene

In this example, a 2:3 mole-mole ratio of p-phenylphenol and p-n-nonyl-phenol, respectively, was substituted for the p-n-nonylphenol of Example 1, above, and the procedure thereof was used herein to produce the product of this Example.

EXAMPLE IV

Preparation of p-Nonyl-Co-p-PhenylCalix[8]arene

In this example, a 5:1 mole-mole ratio for p-n-nonylphenol, respectively, should be substituted for the p-n-nonylphenol of example, above, and the procedure thereof was used herein to produce the product of this Example.

EXAMPLE V

Reaction of P-Nonyl Calix[8]arene With Urea

In this example, a 2-neck flask equipped with magnetic stirrer and a thermometer was charged with 150 parts p-n-nonylcalix[8]arene generated in Example I and 11 parts urea. While mixing the materials were heated to 160° C. for 3 hours under a blanket of nitrogen. The mixture was cooled to ambient temperature and the reaction product extracted using 500 parts n-heptane. The product was isolated by flash removal of solvent as a brownish solid.

EXAMPLE VI

Reaction of p-Nonyl-Co-p-Phenyl Calix[8]arene with Urea

In this example, the reaction product from Example II was substituted for the p-n-nonylphenol of Example I, and the procedure thereof was used herein to produce the product of this Example.

EXAMPLE VII

Reaction of p-Nonyl-Co-p-phenylcalix[8]arene with Urea

In this example, the product from Example III was substituted for the p-n-nonylphenol of Example I, and the procedure thereof was used herein to produce the product of this example.

EXAMPLE VIII

Reaction of p-Nonyl-Co-p-Phenylcalix[8]arene with Urea

In this example, the product from Example IV was substituted for the p-n-nonylphenol of Example I, and the procedure thereof was used herein to produce the product of this example.

EXAMPLE IX

Reaction of p-Nonyl-co-p-Phenylcalix[8]arene with Urea

In this example, the product from Example III was substituted in this Example using 22 parts urea as outlined in Example V to produce the product of this example.

EXAMPLE X

Reaction of p-Nonyl-co-p-Phenylcalix[8]arene with Urea

In this example, the product from Example III was substituted in this example using 33 parts urea as outlined in Example V to produce the product of this example.

EXAMPLE XI

Reaction of p-Nonyl-co-p-Phenylcalix[8]arene with Urea

In this example, the product from Example III was substituted in this example using 44 parts urea as outlined in Example V to produce the product of this Example. The urea addition was made in two equal increments over a heating period of four hours.

EXAMPLE XII

Reaction of p-Nonyl-co-p-Phenylcalix[1]arene with Urea

In this example, the product from Example III was substituted in this Example using 55 parts urea as outlined in Example V to produce the product of this example.

EXAMPLE XIII

Reaction of p-Nonyl-co-p-Phenylcalix[8]arene with Urea

In this example, the product from Example III was substituted in this example using 66 parts urea as outlined in Example V to produce the product of this example.

EXAMPLE XIV

Reaction of p-Nonyl-co-p-PhenylCalix[8]arene with Urea

In this example, the product from Example III was substituted in this example using 77 parts urea as outlined in Example V to produce the product of this example.

EXAMPLE XV

Reaction of p-Nonyl-co-p-PhenylCalix[8]arene with Urea

In this example, the product from Example III was substituted in this Example using 88 parts urea as outlined in Example V to produce the product of this example.

EXAMPLE XVI

Reaction of p-Nonyl-co-p-PhenylCalix[8]arene with Urea

In this example the product from Example III was substituted in this Example using 88 parts urea as outlined in Example V, although the heating time was increased an additional two hours to produce the product of this example.

EXAMPLE XVII

Reaction of p-Nonyl-co-p-PhenylCalix[8]arene with Urea

In this example, the product from Example III was substituted in this example using 88 parts urea as outlined in Examples V, although the heating time was increased an additional four hours to produce the product of this example.

EXAMPLE XVIII

Reaction of p-Nonyl-co-p-PhenylCalix[8]arene with Urea

In this example the product from Example III was substituted in this example using 100 parts urea as outlined in Example V to produce the product of this example.

The materials synthesized according to the present invention were structurally and physically evaluated. The structural property of interest was the detection of allophanates encapsulated within the calixarene matrix which detection was determined using photospectrometric methods. It was fingerprinted by its infrared absorbance at 3412 cm$-1$ (N—H stretch), 1710 cm$-1$ (C=O stretch), and 1160 cm$-1$ (O—C stretch). Results of the diesel fuel solubility and thermal stability of the neat experimental samples are summarized below in Table II.

TABLE II

| Material | Diesel Fuel Solubility at Turbidity Point (wt %) | 50 wt % Decomposition Temperature (deg C.) | 90 wt % Decomposition Temperature (deg C.) |
| --- | --- | --- | --- |
| Unmodified urea | >.1 | 310 | 315 |
| Unmodified biuret | >.1 | 290 | 300 |
| Unmodified triuret | >.1 | 300 | 315 |
| Phenyl allophanate | >.1 | 420 | 920 |
| N-(C9-C14)-allophanate | <15 | | |
| Calix[8]arene-allophanate | <45 | 460 | 960 |
| Calix[8]arene-diallophanate | <45 | 465 | 960 |
| Calix[8]arene-triallophanate | <30 | 480 | 965 |
| Calix[8arene-tetraallophanate | <30 | 460 | 965 |
| Calix[8]arene-pentaallophanate | <30 | 475 | 965 |
| Calix[8]arene-hexaallophanate | <30 | 480 | 945 |
| Calix[8]arene-heptaallophanate | <20 | 480 | 960 |
| Calix[8]arene-octaallophanate | <20 | 480 | 965 |

We claim:
1. A composition of matter comprising a mixture of:
   a) p-nonyl-co-p-phenylcalix[8]arene monoallophanate;
   b) p-nonyl-co-p-phenylcalix[8]arene diallophanate;
   c) p-nonyl-co-p-phenylcalix[8]arene triallophanate;
   d) p-nonyl-co-p-phenylcalix[8]arene tetraallophanate;
   e) p-nonyl-co-p-phenylcalix[8]arene pentallophanate;
   f) p-nonyl-co-p-phenylcalix[8]arene hexaallophanate;
   g) p-nonyl-co-p-phenylcalix[8]arene heptaallophanate; and
   h) p-nonyl-co-p-phenylcalix[8]arene octaallophanate.